Figure 1:
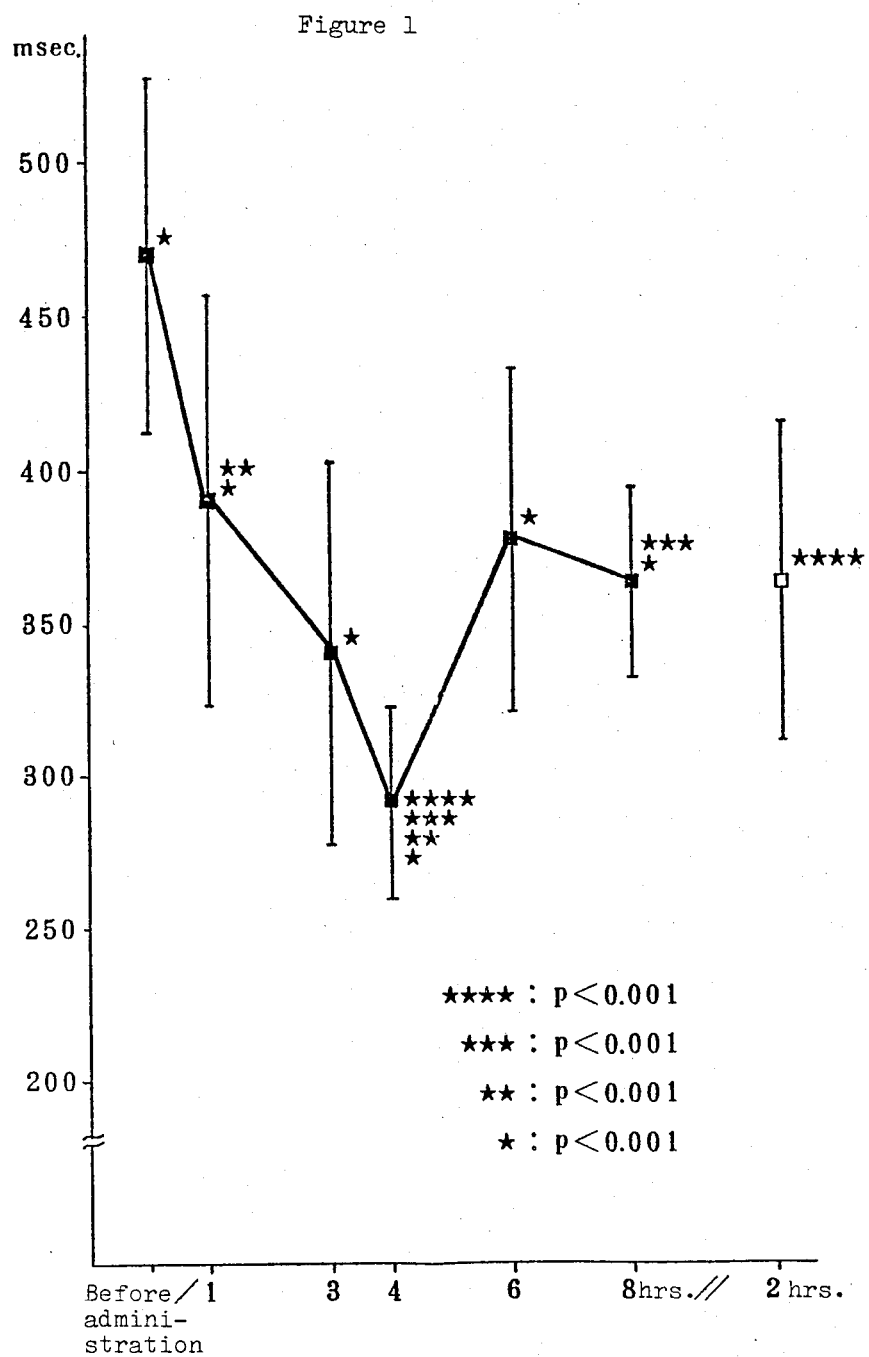

United States Patent [19]

Narabayashi et al.

[11] Patent Number: 4,497,826
[45] Date of Patent: Feb. 5, 1985

[54] ANTIPARKINSONIAN AGENT

[75] Inventors: Hirotaro Narabayashi, 5-12-8, Nakameguro, Meguro-ku, Tokyo-to; Tomoyoshi Kondo, 2-12-3, Sugamo, Toshima-ku, Tokyo-to; Akira Hayashi, 9-5, Tsukumodai 3-chome, Suita-shi, Osaka-fu; Tomokazu Suzuki, 9-30-307, Okamoto 4-chome, Higashinada-ku, Kobe-shi, Hyogo-ken, all of Japan

[73] Assignees: Sumitomo Chemical Company, Limited, Osaka; Hirotaro Narabayashi; Tomoyoshi Kondo, both of Tokyo; Akira Hayashi, Osaka; Tomokazu Suzuki, Hyogo, all of Japan

[21] Appl. No.: 415,907

[22] Filed: Sep. 8, 1982

[30] Foreign Application Priority Data

Sep. 22, 1981 [JP] Japan ................................ 56-150082

[51] Int. Cl.³ .................... A61K 31/15; A61K 31/195
[52] U.S. Cl. ..................................... 514/567; 424/327
[58] Field of Search ............................... 424/319, 327

[56] References Cited

U.S. PATENT DOCUMENTS 3,920,728  11/1975  Hegedus et al. .................... 424/319
4,330,558   5/1982  Suzuki et al. ...................... 424/319

FOREIGN PATENT DOCUMENTS 125630   8/1977  Japan .
1455049 11/1976  United Kingdom .

OTHER PUBLICATIONS

Merck Index, 1976 9th Ed., pp. 136, 228–229.
Archif Fur Psychiatrie und Zeitshrift f. d. ges. Neurologie 203, 560–574 (1962).
Carroll, "Clinical Pharmacology and Therapeutics" 12, 743–761 (1971).
Gunne et al, Scandinav. J. Clin. & Lab. Investigation 18, 425–430 (1966).
Bartholini et al, Biochemical Pharmacology 20, 1243–1247 (1971).
Porter et al, Life Sciences 11, Part I, 787–795 (1972).
Bartholini et al, The Journal of Pharmacology and Experimental Therapeutics 193, 523–532 (1975).
Folia Pharmacol. japon 72, 891–898 (1976).

Primary Examiner—Stanley J. Friedman
Attorney, Agent, or Firm—Birch, Stewart, Kolasch & Birch

[57] ABSTRACT

An antiparkinsonian agent comprising DL- or L-threo-3,4-dihydroxyphenylserine and a decarboxylase inhibitor (e.g. carbidopa and benserazide), which is useful for the treatment of parkinson's disease, particularly treatment of the freezing phenomenon which has not previously been cured by the conventional antiparkinsonian drugs such as L-DOPA.

10 Claims, 4 Drawing Figures

ANTIPARKINSONIAN AGENT

The present invention relates to an antiparkinsonian agent which comprises threo-3,4-dihydroxyphenylserine (hereinafter, referred to as "threo-DOPS") and a decarboxylase inhibitor. The DOPS is a hydroxyamino acid of the formula:

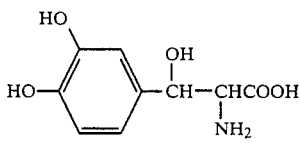

and a salt thereof is included in this invention.

The treatment of parkinson's disease has usually been done by administering L-DOPA (i.e. L-3,4-dihydroxyphenylalanine). It is considered that L-DOPA is converted into dopamine in the brain and thereby remedies the deficiency of dopamine in brain. It has recently been known that when L-DOPA is used together with a decarboxylase inhibitor which acts on the peripheral system, movement of L-DOPA to the central nervous system is enhanced and the therapeutic effect of L-DOPA is thereby enhanced.

As a result of extensive study, the present inventors have found that an agent comprising threo-DOPS and a decarboxylase inhibitor is extremely effective for the treatment of parkinson's disease. That is, it has been found that the agent of the invention is moderately effective on some syndromes of parkinson's disease, such as hardening of the muscle (muscular rigidity, i.e. involuntary stiffening of muscle), and tremors at rest (shaking of extremities, specially at the arm by 4-6 Hz per second). But the most important point is that the agent of the invention is particularly, often dramatically, effective on the symptoms known as the "freezing phenomenon", i.e. the phenomenon that a person can not walk and occasionally falls down because his feet cower as if they are frozen and adhered to the floor. These phenomena also include cowering of the hands resulting in difficulty in writing and cowering of the lip resulting in difficulty in talking. The phenomena have never been modified by the conventional anti-parkinsonian agents including L-DOPA.

The above-described freezing phenomenon tends to appear with progression of the parkinson's disease and is usually observed in old parkinsonian patients with a disease history of more than 5 or 10 years. Such patients show tremendous difficulty in walking, especially in starting, and fall down several times per day due to this phenomenon. Such difficulty troubles daily life, sometimes keeping the patients bedridden.

The agent of the present invention is particularly useful for the treatment of such freezing phenomenon in parkinson's disease which has never been improved by conventional agents.

The present inventors have found that in such old parkinsonian patients, the catecholamine metabolic system in the brain shows a lowering of not only dopamine content but also norepinephrine content. Furthermore, an enzyme for biosynthesis of norepinephrine from dopamine, i.e. dopamine-$\beta$-hydroxylase (hereinafter, referred to as "DBH") shows a decreased activity in the system. Based upon the fact that the present agent is effective in treating the freezing phenomenon in old parkinsonian patients, it is assumed that such freezing phenomenon might result from the lowering of norepinephrine content in the brain and the lowering of DBH activity. Presently, there is neither a report teaching the correlation of the freezing phenomenon with lowering of norepinephrine content in the brain and lowering of DBH activity, nor an idea of the treatment of such a freezing phenomen by compensating the norepinephrine deficiency.

It has long been demonstrated by many researchers that DOPS, a chemically synthetic amino acid, can be decarboxylated by L-aromatic amino acid decarboxylase in vivo and in vitro to form norepinephrine.

Recently four stereoisomers of DOPS were separated and purified, and their enzymatic decarboxylation were elucidated [cf. Bartholini et al, J. Pharmacol. exp. Ther., 193, 523 (1975), and Tanaka et al, Folia Pharmacol. Japan, 72, 891–898 (1976)]. That is, it has been demonstrated that L-isomers (both threo-and erythro-isomers) can be decarboxylated, but D-isomers (both threo- and erythro-isomers) can not be decarboxylated, and further that norepinephrine formed from L-threo-DOPS is confirmed as natural l-norepinephrine, while norepinephrine formed from L-erythro-DOPS is not natural. Thus, L-threo-DOPS is now suggested to be an effective precursor of l-norepinephrine.

Accordingly, it will be understood that the effectiveness of threo-DOPS on parkinson's disease, particularly on freezing phenomenon, will be due to the compensation of norepinephrine in the brain, which is obtained from the conversion of L-threo-DOPS.

The success of therapy with DOPA as a dopamine-precursor therapy in parkinson's disease is no doubt attributable to the properties of L-DOPA, i.e. the capability of penetrating through the so-called Blood-Brain-Barrier (hereinafter, referred to as "B.B.B.") into the cerebral parenchema and being decarboxylated by L-aromatic amino acid decarboxylase to form dopamine which improves the deficiency of dopamine in parkinson's disease. Furthermore, in accordance with the therapy by the combination of DOPA and a decarboxylase inhibitor which has recently been established, the decarboxylase inhibitors inhibit decarboxylation of DOPA in extracerebral tissues, and DOPA can penetrate in a larger amount into the brain, which induces increase of dopamine content in the brain.

Taking into consideration the above mechanism of the DOPA-therapy as a dopamine-precursor therapy, the use of threo-DOPS for the norepinephrine precursor therapy in the central nervous system should be done under the same conditions as in the case of DOPA. That is, DOPS should penetrate through B.B.B. into the cerebral parencheme and should become a good substrate of L-aromatic amino acid decarboxylase in the brain. Since DOPS is a non-physiological amino acid contrary to DOPA, it is not clear whether DOPS has the same properties as DOPA.

Hitherto, reports have been negative concerning whether threo-DOPS can satisfy the above conditions and can be used as a norepinephrine precursor therapy in the central nervous system. For example, it has been reported that the rate of decarboxylation of DL-threo-DOPS was 1/10 smaller than that of DL-erythro-DOPS (cf. Porter et al., Life Sci. Part I, Physiol. Pharmacol., 11, 787, 1972); that the accumulation of norepinephrine in the brain was found to be negligible after intraperitoneal administration of L-threo-DOPS but was remarkable after injection of L-threo-DOPS into a cerebral venticle in experiments using rats, which indicates a poor penetration of L-threo-DOPS through B.B.B. (cf. Bartholini et al., J. Pharmacol. exp. Ther., 193, 523, 1975), and further that a combination of decarboxylase inhibitor and L-threo-DOPS abolished the DOPS-induced rise of norepinephrine in the heart, but it did not enhance the DOPS-induced rise of norepinephrine in the brain in the experiments using rats (cf. Bartholini et al., Biochemical Pharmacology, 20, 1243, 1971).

Negative results were obtained also in clinical test in human by using threo-DOPS. That is, it was reported that the intravenous injection of DL-threo-DOPS (300 mg) to a patient suffering from parkinson's disease was ineffective (cf. W. Birkmayer and O. Hornykiewicz, Arch. Psychiatr., Nevenkr. 203, 560, 1962) and further that the intravenous injection of DL-threo-DOPS (200 mg) to six patients suffering from narcolepsy was ineffective (cf. L. M. Gunne and H. F. Lidwall, Scandinav. J. Clin. and Lab. Investigation, 18, 425, 1966).

In view of the above test results, it has usually been considered in this field that there is almost no possibility for using threo-DOPS as a norepinephrine precursor therapy for treating the parkinson's disease. This view is also stated by B. H. Carroll (cf. Clinical Pharmacology and Therapeutics, 12(5), 743, 1971).

The potential of threo-DOPS as a central nervous system agent has, as stated above, been negatively considered, but the usefulness of threo-DOPS as an agent for treating "peripheral" orthostatic hypotension has recently been revealed in a clinical test by T. Suzuki, A. Hayashi et al, two of the present inventors (cf. U.S. Pat. No. 4,330,558).

It should be noted that potential of erythro-DOPS has, contrary to the case of threo-DOPS, been described with biological data by H. Balthasar et al, as an antihypertensive agent (cf. U.S. Pat. No. 3,920,728).

This indicates that threo-DOPS and erythro-DOPS would have opposite pharmacological activities (i.e. hypertensive and hypotensive, respectively).

Under such a background, it has now surprisingly been found by the present inventors that the combination of threo-DOPS and a peripheral decarboxylase inhibitor is useful for the treatment of parkinson's disease, particularly in the treatment of freezing phenomenon which is occasionally observed in old parkinsonian patients.

An object of the present invention is to provide an important antiparkinsonian agent comprising threo-DOPS and a decarboxylase inhibitor. Another object of the invention is to provide a method for treatment of parkinson's disease, particularly for the remedy of freezing phenomenon in old parkinsonian patients. These and other objects and advantages of the present invention will be apparent to persons skilled in the art from the following description.

The present invention will be illustrated in more detail with reference to the accompanying drawings.

FIG. 1 shows the change of speed in response with lapse of time when a combination of DL-threo-DOPS and carbidopa is administered (measured at the filled square point). The abscissa axis represents time (hour) after administration, and the ordinate axis means transit time (msec). The filled squares represent the transit time after DL-threo-DOPS intake and the open squares on the right side represent the transit time 2 hours after administation of L-DOPA, benserazid hydrochloride and trihexyphenidyl hydrochloride.

Figure 2:
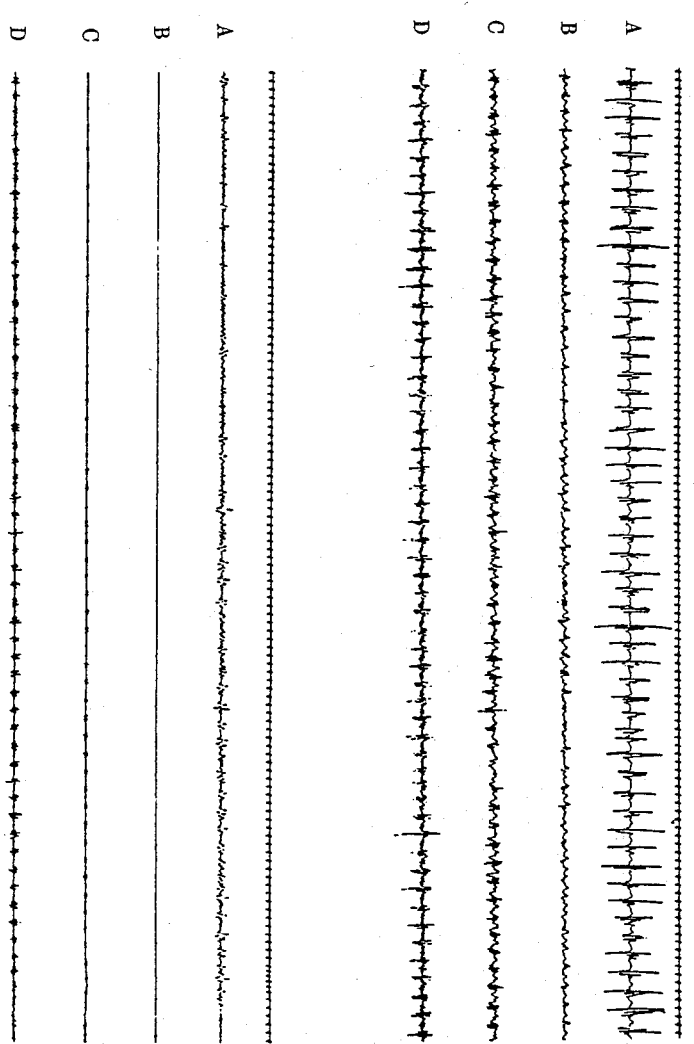
Figure 3:
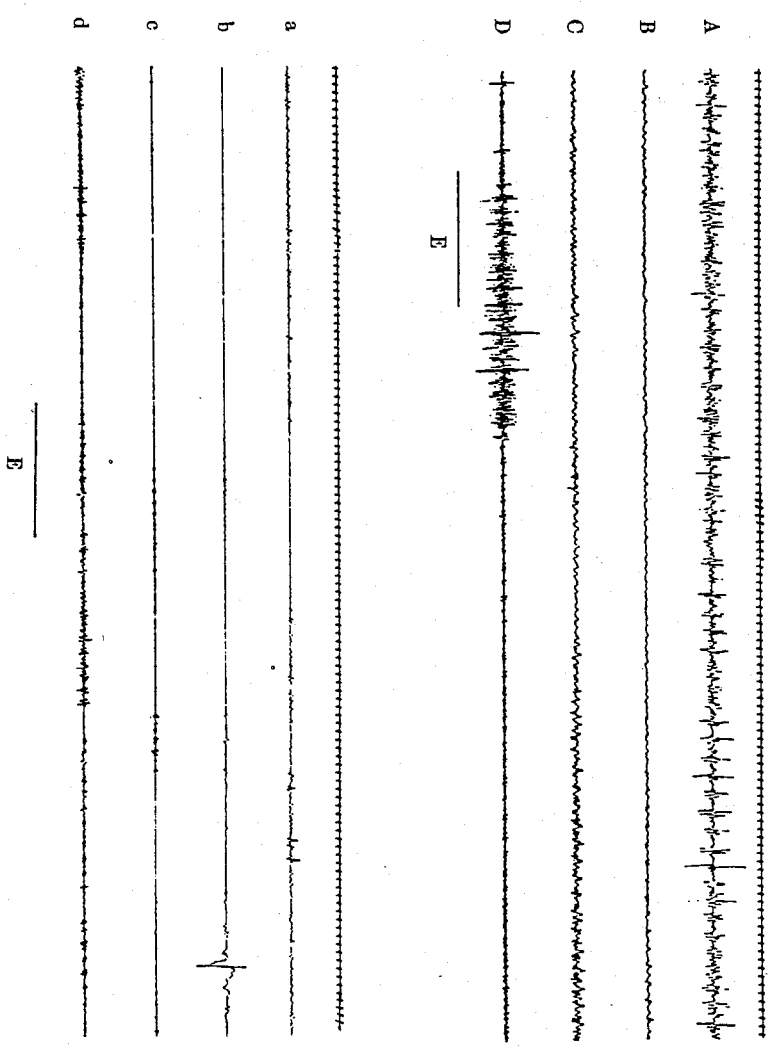
Figure 4:
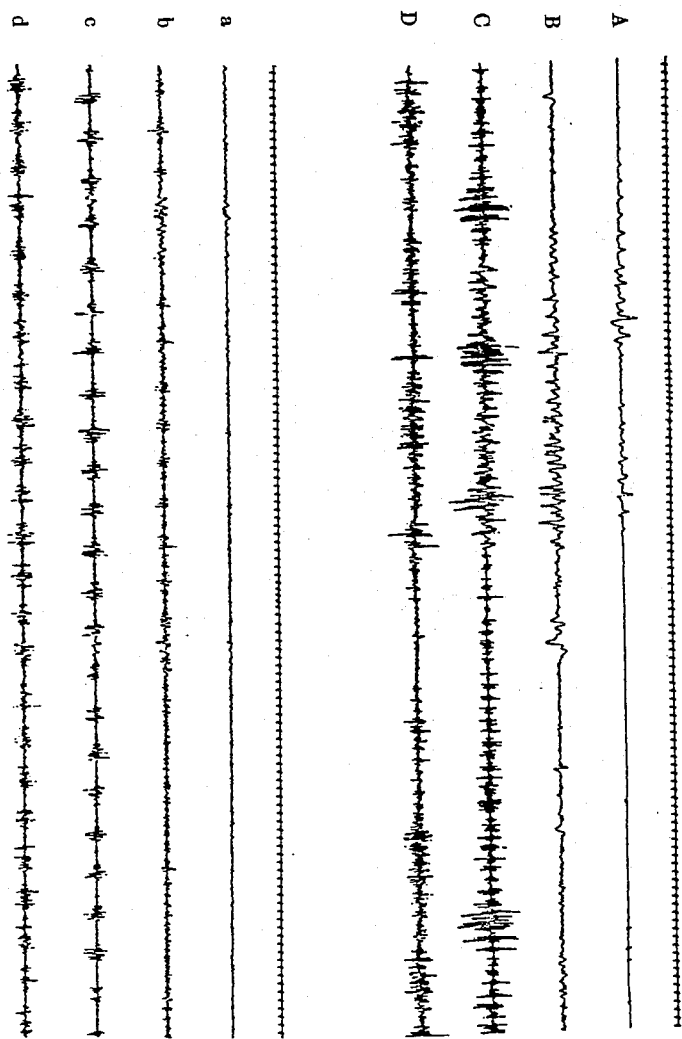

FIGS. 2, 3 and 4 each show surface electromyograms after DL-threo-DOPS and carbidopa were administered in comparison with the surface electromygrams before administration of the drugs. The data of FIG. 2 relate to a tremor of the right upper arm at static state. The data of FIG. 3 relate to tonic stretch reflexes of the extensor muscle of right forearm. The data of FIG. 4 indicate improvement of the skillfulness when flexion and extension movement at the right wrist joint was tried. In these figures, A is an electromyogram of a biceps muscle of the right upper arm, B is an electromyogram of a triceps muscle of the right upper arm, C is an electromyogram of a flexor muscle of the forearm, and D is an electromyogram of an extensor muscle of the forearm, all these data being before administration of the drugs; and a, b, c and d are the electromygrams of each corresponding portions after administration of the drugs. E in FIG. 3 represents the period of passive stretching.

The agent for treatment of parkinson's disease of the present invention comprises threo-DOPS and a decarboxylase inhibitor.

Threo-DOPS per se is known and includes DL-threo-DOPS and L-threo-DOPS, which can be prepared by known processes, for example, the processes disclosed in Japanese Patent Publication (unexamined) No. 19931/1979 and No. 29551/1981. Threo-DOPS may be used in the form of a free base or in the form of an acid addition salt thereof. The acids suitable for forming the acid addition salt are for example inorganic acids (e.g. hydrochloric acid, hydrobromic acid, sulfuric acid, etc.) and organic acids (e.g. fumaric acid, citric acid, tartaric acid, succinic acid, etc.).

The decarboxylase inhibitor used together with threo-DOPS includes all conventional decarboxylase inhibitors, for example, carbidopa (i.e. S-$\alpha$-hydrazino-3,4-dihydroxy-$\alpha$-methylbenzenepropanoic acid monohydrate), benserazide (i.e. DL-serin 2-[2,3,4-trihydroxyphenyl)methyl]hydrazide) or its hydrochloride, methyldopa (i.e. L-$\alpha$-methyl-3,4-dihydroxyphenylalanine) or the like. One or more of these decarboxylase inhibitors can be combined with threo-DOPS.

The threo-DOPS and decarboxylase inhibitor of the present invention are usually administered to the patient orally or parenterally and are usually used in the form of a pharmaceutical composition which contains the two compounds in an effective and non-toxic amount in admixture with conventional pharmaceutical carrier materials suitable for oral or parenteral application and being unreactive with the active compounds. The pharmaceutical composition may be in the dosage form of tablets, capsules, granules, fine granules, powders, syrups, suspensions, emulsions, suppositories, injections, or the like. These pharmaceutical compositions can be prepared by conventional methods by using conventional carrier materials, excipients, binding agents, stabilizers, etc. For injection, the preparation may be prepared by dissolving the active compounds in purified water for injection, which may optionally contain other additives, such as isotonic agents (e.g. glucose, saline), buffering agents, solubilizers, pH adjusting agents, preservatives, or the like.

The dosage of threo-DOPS may vary with the administration routes, the age and weight of the patient, the kinds and severity of the diseases to be treated, or the like. In case or oral administration in adult, it is usually used in an amount of 0.1 to 4 g per day, which may be administered once a day but may also be divided and administered two to several times per day. In case of intravenous injection in an adult, it is usually used in an amount of 0.1 to 1 g per day, and may be administered once a day but may also be divided and administered in two to several times per day.

The decarboxylase inhibitors may be used in a wide ratio range with respect to threo-DOPS, but are usually used in a ratio of from 0.025 to 0.5 mole to 1 mole of threo-DOPS.

The threo-DOPS has very weak toxicity. The $LD_{50}$ in mice is more than 10 g/kg p.o., and about 10 g/kg i.p., and hence, there is no harmful side effect in the dosage of the present invention. In fact, serious side effects were not observed in the clinical tests.

The agent of the present invention may optionally be used together with the conventional anti-parkinsonian drugs, such as L-DOPA, trihexyphenidyl hydrochloride (i.e. 3-(1-piperidyl)-1-cyclohexyl-1-phenyl-1-propanol hydrochloride), procyclidine hydrochloride (i.e. 1-cyclohexyl-1-phenyl-3-pyrrolidino-1-propanol hydrochloride), biperidine (i.e. α-5-norbornen-2-yl-α-phenyl-1-piperidino-propanol), amantadine hydrochloride and the like.

The effect of the present agent is illustrated by the following clinical tests.

CLINICAL TEST 1

The patient was a man (68 years old) suffering from parkinson's disease, having a disease history of 12 years after being affected by the disease. The primary clinical features were moderate rigidity of the four limbs and trunk were slight tremor. At about 6 years after the start of the disease, L-DOPA therapy was started. This therapy improved the stiffness and tremor remarkably, and the behavior in daily life became almost normal so that the patient returned to work as a manager of a stock company.

Thus, the patient was successfully treated for several years with L-DOPA (400 mg), benserazide hydrochloride (100 mg as a free benserazide) and trihexyphenidyl hydrochloride (tradename: Artane, 6 mg) by oral administration daily by which the stiffness and tremor were improved. However, about two years ago, the patient started to show freezing in gait, which became worse with time, and during this year the patient tended to fall down several times a day and could not walk by himself. The patient also had difficulty in writing. When an increased amount of L-DOPA was administered aiming to improve such freezing, it became worse.

This patient was then treated with DL-threo-DOPS in the following dosage, while keeping the administration of L-DOPA, the decarboxylase inhibitor (benserazide hydrochloride) and trihexyphenidyl hydrochloride at strictly the same dosage throughout the period of trial.

Dosage

DL-threo-DOPS was orally administered to the patient in the form of a capsule (DL-DOPS content: 200 mg) as follows:

| First to 2nd day | 6 capsules per day |
| --- | --- |
| 3rd to 4th day | 9 capsules per day |
| 5th to 6th day | 12 capsules per day |

It is noted that the decarboxylase inhibitor was not newly administered, because it was already administered together with L-DOPA.

Clinical Results

At the 3rd day after initiation of the treatment with DL-threo-DOPS, the patient showed more active behavior and expression, was speaking more clearly than before, and the difficulty in writing had disappeared. As to walking, it became much easier at the 3rd day of the treatment, while even one step was almost impossible before the treatment; on the 5th day the patient could walk smoothly without any assistance and the steps of the walk became almost normal with wide steps, which resulted in no falling down during walking within rooms and passageways. Thereafter, the administration of DL-threo-DOPS was maintained with a reduced dose of 9 capsules per day and the improvement of the syndrome is still continuing.

CLINICAL TEST 2

The patient was a man (73 years old) suffering from parkinson's disease, whose main syndrome was "pure akinesia" which was first described by one of the present inventors [Narabayashi et al, Advances in Parkinsonism (eds., W. Birkmayer and O. Hornykiewicz) Roche Basle, pages 335–342 (1976)]. This patient did not show any muscle stiffness or tremor, and hence, therapy with L-DOPA or trihexyphenidyl hydrochloride was not applied to him.

This patient showed mainly freezing in walking, could not step out at a flat place and occasionally fell down. The trouble with walking appeared significantly on flat floors and on the road, particularly on a narrow road, entrance or exit in a station, entrance or exit of room, or the like, where even one step was impossible. But on the other hand, motion such as going up or down the stairs could be done rather normally. Accordingly, such a syndrome is also called paradoxical kinesia.

The patient was treated with DL-threo-DOPS and a decarboxylase inhibitor (carbidopa) in the same dosage as in the above Clinical Test 1. When the dose of the drugs was increased to 9 capsules (1,800 mg) of DL-threo-DOPS and 90 mg of carbidopa, the walking was improved and the freezing in walking disappeared. Several days after the dose of drugs was reached to the above, the walking became almost normal.

CLINICAL TESTS 3 to 7

In the above clinical tests, the agent of the present invention showed remarkable effect particularly on freezing phenomenon and showed also mild or moderate effects on other syndromes of parkinson's disease such as muscle stiffness and tremor.

In the same manner, other patients as shown in Table 1 were treated with threo-DOPS and a decarboxylase inhibitor. The results are shown in Table 1 together with the data in the above Clinical Tests 1 and 2.

TABLE

| | Clinical test No. | | | | | | |
| --- | --- | --- | --- | --- | --- | --- | --- |
| | 1 | 2 | 3 | 4 | 5 | 6 | 7 |
| Age | 57 | 73 | 58 | 53 | 47 | 74 | 57 |

TABLE-continued

| | Clinical test No. | | | | | | |
|---|---|---|---|---|---|---|---|
| | 1 | 2 | 3 | 4 | 5 | 6 | 7 |
| Sex | male | male | male | female | female | male | male |
| Dose (mg) of DL-threo-DOPS | 2400 | 1800 | 1200 | 1600 | 1200 | 1200 | 1200 |
| Decarboxylase inhibitor (Dose: mg) | b (100) | c (90) | b (112.5) | c (60) | b (125) | c (90) | c (90) |
| Drug used together (dose: mg) | L-DOPA (400) + t (6) | — | L-DOPA (450) + t (6) | L-DOPA (600) + t (6) | L-DOPA (500) + t (6) | — | — |
| Evaluation Totally | A | A | B | C | B | B | C |
| Freezing in Walking | A | A | A | C | B | A | * |
| Freezing in Speaking | A | A | A | C | * | B | D |
| Freezing in Writing | A | A | B | C | * | C | C |
| Mortionless | A | * | B | C | B | A | C |
| Muscle stiffness | B | * | B | * | * | B | C |
| Tremor | B | * | B | * | A | B | C |
| Mental activity | A | A | B | C | * | A | C |

Abbreviation of the drugs listed in Table 1:
b benserazide (dose: as free benserazide)
c carbidopa
t trihexyphenidyl hydrochloride (Artane ®)
Abbreviation of evaluation of effect in Table 1:
A Remarkable improvement of syndrome
B Moderate improvement of syndrome
C Mild improvement of syndrome
D Ineffective or no improvement
*No syndrome was observed before the treatment with DL-threo-DOPS, or the syndrome disappeared by the treatment with other antiparkinsonian drugs.

Improvement in Speed of Response

In order to quantitatively analyze the improvement of the syndromes in the above clinical tests, a speed of response was measured as to some patients in the tests.

Method for the measurement: The transit time was measured by using two switches (distance: 15 cm) in the same manner as described in Masao Kato and Kazuya Ando, "Parkinson's Disease, Physiopathology and Therapy", page 106, issued by Kanehara Shuppan on Mar. 31, 1978.

Results: The data of the patient in the above Clinical Test 6 are shown in the attached FIG. 1. As is shown in the figure, when it was measured before administration of DL-threo-DOPS (600 mg) and carbidopa (60 mg) and 1, 3, 4, 6 and 8 hours after the administration, the effect peaked at 4 hours after administration, and at the same time, the transit time was shortened about 170 msec as compared to that before administration of the drugs. It was also shorter than the transit time measured at 2 hours after administration of L-DOPA (100 mg), benserazide hydrochloride (25 mg as benserazide) and trihexyphenidyl hydrochloride (2 mg).

Improvement in Surface Electromyogram

As to the patient in the above Clinical Test 6, the effect of administration of DL-threo-DOPS (600 mg) and carbidopa (60 mg) was measured by surface electromyogram, which was compared with that measured before the administration of drugs.

(1) Improvement of tremor of the right upper arm at the static state is shown in the attached FIG. 2.

Evaluation: the tremor was remarkably decreased or improved.

(2) Improvement of stiffness of the extensor muscle of the right forearm and quantitative change of tonic stretch reflex are shown in the attached FIG. 3.

Evaluation: the tonic stretch reflex was reduced, that is, the rigidity of the muscle was remarkably decreased and improved.

(3) Skillfulness, when flextion and extention movement is repeatedly performed at the right wrist joint, is shown in the attached FIG. 4.

Evaluation: It was remarkably improved.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for treating parkinson's disease, which comprises administering a pharmaceutically effective amount of DL- or L-threo-3,4-dihydroxyphenylserine or a pharmaceutically acceptable acid addition salt thereof and from about 0.025 to about 0.50 mole to 1 mole of said DL- or L-threo-3,4-dihydroxyphenylserine of a decarboxylase inhibitor selected from the group consisting of carbidopa, benserazide, the hydrochloride of benserazide and methyldopa to a patient suffering from parkinson's disease.

2. A method according to claim 1, wherein said DL- or L-threo-3,4-dihydroxyphenylserine or said salt thereof is orally administered in an amount of from about 0.1 to 4 g per day.

3. A method according to claim 1, wherein said threo-3,4-dihydroxyphenylserine or said salt thereof is intravenously administered in an amount of from about 0.1 to 1 g per day.

4. A method according to claim 1, 2 or 3, wherein the decarboxylase inhibitor is carbidopa, benserazide or the hydrochloride benserazide.

5. A method for treating parkinson's disease in a patient for whom treatment with L-DOPA and a decarboxylase inhibitor is substantially ineffective, which comprises administering a pharmaceutically effective amount of DL- or L-threo-3,4-dihydrophenylserine or a pharmaceutically acceptable acid addition salt thereof and a decarboxylase inhibitor selected from the group consisting of carbidopa, benserazide, the hydrochloride of benserazide and methyldopa to a patient suffering from parkinson's disease, said decarboxylase inhibitor being used in an amount of 0.025 to 0.5 mole to 1 mole of the DL- or L-threo-3,4-dihydroxyphenylserine.

6. A method according to claim 5, wherein DL- or L-threo-3,4-dihydroxyphenylserine or said salt thereof is orally administered in an amount of from 0.1 to 4 g per day.

7. A method according to claim 5, wherein said threo-3,4-dihydrophenylserine is intravenously administered in an amount of from about 0.1 to 1 g per day.

8. A method according to claim 5, 6 or 7, wherein the decarboxylase inhibitor is carbidopa, benserazide or the hydrochloride of benserazide.

9. An antiparkinsonian pharmaceutical composition comprising a pharmaceutically effective amount of DL- or L-threo-3,4-dihydroxyphenylserine or a pharmaceutically acceptable acid addition salt thereof and a decarboxylase inhibitor selected from the group consisting of carbidopa, benserazide, the hydrochloride of benserazide and methyldopa, said decarboxylase inhibitor being contained in an amount of from about 0.025 to about 0.5 mole to 1 mole of said DL- or L-threo-3,4-dihydroxyphenylserine.

10. A composition according to claim 9, wherein said decarboxylase inhibitor is carbidopa benserazide or the hydrochloride of benserazide.

* * * * *